(12) United States Patent
Ikegami et al.

(10) Patent No.: US 11,555,950 B2
(45) Date of Patent: Jan. 17, 2023

(54) TRANSPARENT ARTICLE

(71) Applicant: NIPPON ELECTRIC GLASS CO., LTD., Shiga (JP)

(72) Inventors: Koji Ikegami, Otsu (JP); Toshiyuki Kajioka, Otsu (JP)

(73) Assignee: Nippon Electric Glass Co., Ltd., Shiga (JP)

( * ) Notice: Subject to any disclaimer, the term of this patent is extended or adjusted under 35 U.S.C. 154(b) by 832 days.

(21) Appl. No.: 16/468,186

(22) PCT Filed: Dec. 11, 2017

(86) PCT No.: PCT/JP2017/044316
§ 371 (c)(1),
(2) Date: Jun. 10, 2019

(87) PCT Pub. No.: WO2018/110486
PCT Pub. Date: Jun. 21, 2018

(65) Prior Publication Data
US 2019/0391303 A1    Dec. 26, 2019

(30) Foreign Application Priority Data

Dec. 12, 2016  (JP) .............................. JP2016-240726

(51) Int. Cl.
*G02B 5/02*    (2006.01)
*G01N 21/55*   (2014.01)
(Continued)

(52) U.S. Cl.
CPC ........... *G02B 5/0278* (2013.01); *G01N 21/55* (2013.01); *G01N 33/386* (2013.01); *G01N 2021/177* (2013.01); *G01N 2021/555* (2013.01)

(58) Field of Classification Search
CPC .. G02B 5/0221; G02B 5/0278; G02B 5/0268; G02B 1/11; G02B 1/115; G02B 5/0294; G02B 5/0215; G02B 1/14; G02B 1/18; G02B 5/0247; G02B 1/113; G02B 5/0205; G02B 5/0226; G02B 1/12; G02B 5/0231;
(Continued)

(56) References Cited

U.S. PATENT DOCUMENTS 3,989,348 A  *  11/1976  Hudson ................. G02B 27/40
                                                    359/209.1
4,443,088 A  *   4/1984  Ohtaka ................. G02B 5/045
                                                    359/743
(Continued)

FOREIGN PATENT DOCUMENTS

CN    101839689 A  *  9/2010   ............. G02B 27/40
CN    103502166 A     1/2014
(Continued)

OTHER PUBLICATIONS

Japanese Office Action dated Dec. 7, 2021, Japanese Patent Application No. 2018-556656.
(Continued)

*Primary Examiner* — Michael P Stafira
(74) *Attorney, Agent, or Firm* — Cesari & McKenna, LLP

(57) ABSTRACT

A glass article (10) as a transparent article has a haze value of 15% or less and a clarity value of 9% or less. Preferably, the product of the haze value, the clarity value, and the sparkle value is 0.5 or less.

4 Claims, 2 Drawing Sheets

(51) Int. Cl.
*G01N 33/38* (2006.01)
*G01N 21/17* (2006.01)

(58) Field of Classification Search
CPC ....... G02B 5/0242; G02B 1/118; G02B 1/111;
G02B 21/367; G02B 2207/101; G02B
27/4205; G02B 27/4272; G02B 5/287;
G02B 5/02; G02B 5/208; G02B 5/0284;
G02B 27/01; G02B 27/48; G02B 3/0087;
G02B 5/00; G02B 5/0263; G02B
2027/014; G02B 2027/0178; G02B
2027/0187; G02B 27/0093; G02B 27/017;
G02B 21/06; G02B 21/14; G02B
21/0032; G02B 21/008; G02B 21/10;
G02B 21/006; G02B 21/02; G02B
21/084; G02B 27/40; G02B 21/0036;
G02B 21/0092; G02B 21/0076; G02B
21/24; G02B 3/0056; G02B 21/086;
G02B 21/361; G02B 27/30; G02B
3/0043; G02B 21/082; G02B 27/0927;
G02B 27/0994; G02B 21/0016; G02B
21/16; G02B 27/1006; G02B 27/141;
G02B 5/0236; G02B 5/20; G02B
19/0071; G02B 27/144; G02B 19/0066;
G02B 21/125; G02B 21/245; G02B
21/32; G02B 21/33; G02B 21/34; G02B
21/365; G02B 27/0172; G02B 27/02;
G02B 27/0922; G02B 27/102; G02B
27/145; G02B 5/003; G02B 5/021; G02B
5/045; G02B 5/24; G02B 6/0003; G02B
6/001; G02B 6/12002; G02B 6/4298;
G01N 21/55; G01N 21/87; G01N 33/381;
G01N 2201/06146; G01N 2201/0634;
G01N 21/255; G01N 15/06; G01N
2015/0693; G01N 2021/8416; G01N
2021/8578; G01N 2021/8592; G01N
21/53; G01N 21/85; G01N 2021/4735;
G01N 21/256; G01N 21/274; G01N
21/474; G01N 21/4785; G01N 21/57;
G01N 21/25; G01N 21/4738; G01N
2021/177; G01N 2021/555; G01N
33/386; G01N 2021/4711; G01N
2021/575; G01N 33/32; G01N
2021/8427; G01N 2033/0096; G01N
21/27; G01N 21/8422; G01N 21/17;
G01N 21/8806; G01N 2021/1776; G01N
2021/8819; G01N 21/49; G01N
2201/063; G01N 15/0227; G01N
15/1434; G01N 15/1475; G01N
2015/1006; G01N 15/1493; G01N
2021/335; G01N 21/253; G01N 21/33;
G01N 21/41; G01N 21/88; G01N
21/9501; G01N 21/956; G01N 21/95684;
G01N 2201/061; G01J 3/02; G01J
3/0205; G01J 3/0208
See application file for complete search history.

(56) References Cited

U.S. PATENT DOCUMENTS

| | | | |
|---|---|---|---|
| 8,598,771 | B2 | 12/2013 | Carlson et al. |
| 9,734,590 | B2 | 8/2017 | Prakash |
| 2007/0217015 | A1 | 9/2007 | Furuya et al. |
| 2011/0062849 | A1* | 3/2011 | Carlson ............... C03C 15/00 428/141 |
| 2012/0218640 | A1 | 8/2012 | Gollier et al. |
| 2013/0107370 | A1* | 5/2013 | Lander ............... C03C 3/093 359/609 |
| 2016/0326047 | A1 | 11/2016 | Mototani |
| 2017/0176254 | A1* | 6/2017 | Ehbets ............... G01N 21/255 |
| 2017/0285227 | A1 | 10/2017 | Chen et al. |
| 2017/0327418 | A1 | 11/2017 | Gollier et al. |
| 2018/0038995 | A1 | 2/2018 | Fujii |
| 2018/0170800 | A1 | 4/2018 | Takeda |
| 2019/0248703 | A1 | 8/2019 | Gollier et al. |
| 2020/0180210 | A1 | 6/2020 | Kajioka |
| 2020/0191999 | A1 | 6/2020 | Kajioka et al. |
| 2020/0197978 | A1 | 6/2020 | Kajioka et al. |
| 2021/0116607 | A1 | 4/2021 | Kajioka et al. |
| 2022/0043184 | A1 | 2/2022 | Saitoh |

FOREIGN PATENT DOCUMENTS

| | | | | |
|---|---|---|---|---|
| CN | 104834034 | A | 8/2015 | |
| CN | 105319616 | A | 2/2016 | |
| DE | 112014000995 | T5 * | 11/2015 | ............ G01J 3/463 |
| EP | 3 505 979 | A1 | 3/2019 | |
| JP | 10-221506 | A | 8/1998 | |
| JP | 2002/189107 | A | 7/2002 | |
| JP | 2003/222713 | A | 8/2003 | |
| JP | 2007/041514 | A | 2/2007 | |
| JP | 2007/187952 | A | 7/2007 | |
| JP | 2010/064932 | A | 3/2010 | |
| JP | 2011/047982 | A | 3/2011 | |
| JP | 2012/051175 | A | 3/2012 | |
| JP | 2012/093570 | A | 5/2012 | |
| JP | 2013504514 | A | 2/2013 | |
| JP | 2014038362 | A * | 2/2014 | ............ G02B 1/105 |
| JP | 2014/059334 | A | 4/2014 | |
| JP | 2014/513029 | A | 5/2014 | |
| JP | 2015/196303 | A | 11/2015 | |
| JP | 2016/5839134 | B2 | 1/2016 | |
| JP | 2016/018068 | A | 2/2016 | |
| JP | 2016/6013378 | B2 | 10/2016 | |
| JP | 2017/538150 | A | 12/2017 | |
| JP | 2018/077279 | A | 5/2018 | |
| TW | 2017/010064 | A | 3/2017 | |
| WO | WO-2003/3060573 | A2 | 7/2003 | |
| WO | WO-2008020548 | A1 * | 2/2008 | ............ B82Y 20/00 |
| WO | WO-2012/118594 | A1 | 9/2012 | |
| WO | WO-2013142084 | A1 * | 9/2013 | ........... G02B 3/0043 |
| WO | WO-2014/119453 | A1 | 8/2014 | |
| WO | WO-2015092048 | A1 * | 6/2015 | ............ C08K 3/22 |
| WO | WO-2015/137196 | A1 | 9/2015 | |
| WO | WO-2015/163328 | A1 | 10/2015 | |
| WO | WO-2015163330 | A1 * | 10/2015 | ............ G02B 5/02 |
| WO | WO-2015199026 | A1 * | 12/2015 | ............ G02B 5/00 |
| WO | WO-2015199796 | A2 * | 12/2015 | ............ B05D 1/28 |
| WO | 2016069113 | A1 | 5/2016 | |
| WO | WO-2016/068112 | A1 | 5/2016 | |
| WO | WO-2016069113 | A1 * | 5/2016 | ............ G02B 1/12 |
| WO | WO-2016088850 | A1 * | 6/2016 | ............ B32B 27/18 |
| WO | WO-2016158780 | A1 * | 10/2016 | ............ C12M 1/34 |
| WO | WO-2016/181983 | A1 | 11/2016 | |
| WO | WO-2016190138 | A1 * | 12/2016 | ............ C08F 297/02 |

OTHER PUBLICATIONS

Cohen et al, "Surface Roughness and Texture: Considerations when Making the Change from R Parameters to S Parameters," Finishing & Coating website, Mar. 9, 2021, available at https://finishingandcoating.com/index.php/plating/567-surface-roughness-and-texture-considerations-when-making-the-change-from-rparameters-to-s-parameters, 12 pages.

Klapetek et al., "Gwyddion User Guide," 2012, 11 pages.

* cited by examiner

TRANSPARENT ARTICLE

TECHNICAL FIELD

The present invention relates to a transparent article.

BACKGROUND ART

In order to improve visual recognition of a display device, the application of an antireflection layer or an anti-glare layer to the display surface of the display device has been suggested. For example, patent document 1 describes that when an antireflection film including a low refractive layer is applied to a base material and the main surface of the low refractive layer undergoes an anti-glare process, the antireflection film will have an anti-glare function in addition to an antireflection function.

PRIOR ART LITERATURE

Patent Literature

Patent Document 1: Japanese Laid-Open Patent Publication No. 10-221506

SUMMARY OF THE INVENTION

Problem to be Solved by the Invention

The inventors of the present invention have conducted extensive studies and found that a person will perceive that an image viewed through a transparent article such as a glass article would be easier to view if the transparent article has a haze value and a clarity value that are respectively in a certain range.

One object of the present invention is to provide a transparent article that allows a person to perceive that an image is easily viewed through the transparent article.

Means for Solving the Problem

A transparent article that solves the above problem includes a first main surface located at a front side and a second main surface located at a rear side. The transparent article has a haze value of 15% or less that is specified by JIS K7136 (2000) and a clarity value of 9% or less.

A transparent article that solves the above problem includes a first main surface located at a front side and a second main surface located at a rear side. The transparent article has a sparkle value of 0.02 or less and a clarity value of 9% or less.

In the above transparent article, it is preferred that the product of the haze value, clarity value, and sparkle value be 0.5 or less.

The clarity value is a ratio of a brightness of a specular reflection component to a brightness of a total refection light obtained from brightness distribution data of an image, which is a reflection of a light source on the first main surface of the transparent article.

The sparkle value is a value obtained by arranging a planar light source at a position opposing the second main surface of the transparent article, arranging a pattern mask of 500 pixels per inch (ppi) between the transparent article and the planar light source, imaging the transparent article from a position opposing the first main surface so that the first main surface of the transparent article and a top surface of the pattern mask are included in a depth of field having a permissible circle of confusion diameter of 53 μm, calculating an average value and a standard deviation of a pixel brightness of the pattern mask by analyzing the image data obtained through the imaging, and dividing the standard deviation by the average value.

Effect of the Invention

The present invention succeeds in allowing a person to perceive that an image is easily viewed through the transparent article.

MODE FOR CARRYING OUT THE INVENTION

One embodiment of the present invention will now be described.

Figure 1:
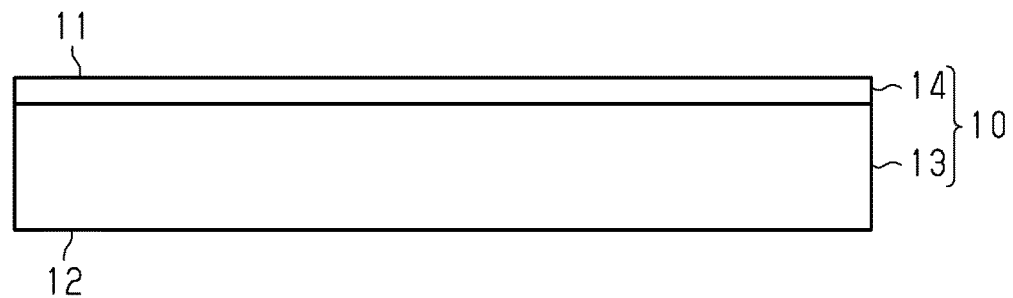
FIG. 1 is a schematic view of a glass article.

As shown in FIG. 1, a transparent article is a glass article 10 that is a sheet or a plate including a first main surface 11 located at a front side and a second main surface 12 located at a rear side. The glass article 10 is, for example, arranged on a display surface of a display device when in use. The glass article 10 may be a member coupled to a display surface of a display device. That is, the glass article 10 may be a member retrofitted to a display device.

As shown in FIG. 1, the glass article 10 includes a light-transmissive base material layer 13 that is made of glass. The base material layer 13 has a thickness of, for example, 0.5 to 1.3 mm. The glass forming the base material layer 13 may be, for example, a known glass such as an alkali-free glass, an alumino-silicate glass, soda lime glass, or a chemically reinforced glass. Among these known glasses, it is preferred that an alumino-silicate glass be used. The use of a reinforced glass including 50 to 80% by mass of $SiO_2$, 5 to 25% by mass of $Al_2O_3$, 0 to 15% by mass of $B_2O_3$, 1 to 20% by mass of $Na_2O$, and 0 to 10% by mass of $K_2O$ is particularly preferred.

One surface of the base material layer 13 includes a light-transmissive anti-glare layer 14 having a structure in which uneven spots are scattered. The structure in which uneven spots are scattered refers to a structure that includes insular bulged portions and flat portions arranged therebetween. The first main surface 11 of the glass article 10 is the side on which the anti-glare layer 14 is arranged. The uneven spots are not shown in FIG. 1.

The anti-glare layer 14 has a thickness in a range of, for example, 40 to 500 nm. The structure of the anti-glare layer 14 in which uneven spots are scattered is formed, for example, by a matrix including $SiO_2$, $Al_2O_3$, $ZrO_2$, and $TiO_2$. Preferably, the insular bulged portions of the anti-glare layer 14 have a height of, for example, 200 to 500 nm. Preferably, the bulged portions have a diameter (average particle diameter) of, for example, 1 to 20 μm. It is preferred that 30% to 70% of the anti-glare layer 14 be the flat portions, which are portions other than the bulged portions.

The anti-glare layer 14 may be formed by applying a coating agent to the base material layer 13 and heating the coating agent. The coating agent includes, for example, a matrix precursor and a liquid medium that melts the matrix precursor. Examples of the matrix precursor in the coating agent include inorganic precursors such as silica precursors, alumina precursors, zirconia precursors, and titania precursors. A silica precursor is preferred because it decreases an anti-glare refractive index and facilitates control of the reactivity.

Examples of the silica precursor include silane compounds including a hydrolyzable group and a hydrocarbon group bound to a silicon atom, a hydrolytic condensate of a silane compound, and a silazane compound. It is preferred that at least one of or both of a silane compound and a hydrolytic condensate thereof be included to adequately limit cracking in the anti-glare layer 14 even when the anti-glare layer 14 is formed to be thick.

The silane compound includes a hydrolyzable group and a hydrocarbon group bound to a silicon atom. The hydrocarbon group may include a group selected from or a combination of two or more of —O—, —S—, —CO—, and —NR'— (R' is hydrogen atom or univalent hydrocarbon group) between carbon atoms.

The hydrocarbon group may be a univalent hydrocarbon group bound to one silicon atom or a divalent hydrocarbon group bound to two silicon atoms. Examples of the univalent hydrocarbon group include alkyl groups, alkenyl groups, and aryl groups. Examples of the divalent hydrocarbon group include alkylene groups, alkenylene groups, and arylene groups.

Examples of the hydrolyzable group include alkoxy groups, acyloxy groups, ketoxime groups, alkenyloxy groups, amino groups, aminooxy groups, amido groups, isocyanate groups, and halogen atoms. An alkoxy group, an isocyanate group, and a halogen atom (particularly, chlorine atom) are preferred since they are well-balanced in terms of stabilizing the silane compound and facilitating hydrolysis of the silane compound. The alkoxy group is preferably an alkoxy group with 1 to 3 carbons, and further preferably a methoxy group or an ethoxy group.

Examples of the silane compound include alkoxysilanes (such as tetramethoxysilane, tetraethoxysilane, and tetraisopropoxysilane), alkoxysilanes including an alkyl group (such as methyltrimethoxysilane and ethyltrimethoxysilane), alkoxysilanes including a vinyl group (such as vinyltrimethoxysilane and vinyltriethoxysilane), alkoxysilanes including an epoxy group (such as 2-(3,4-epoxycyclohexyl) ethyltrimethoxysilane, 3-glycidoxypropyltrimethoxysilane, 3-glycidoxypropylmethyldiethoxysilane, and 3-glycidoxypropyltriethoxysilane), and alkoxysilanes including an acryloyloxy group (such as 3-acryloyloxypropyltrimethoxysilane). Among these silane compounds, the use of at least one of or both of an alkoxysilane and a hydrolytic condensate thereof is preferred, and the use of a hydrolytic condensate of an alkoxysilane is further preferred.

The silazane compound is a compound including a bond of silicon and nitrogen (—SiN—). The silazane compound may be a low-molecular compound or a high-molecular compound (polymer having predetermined repeating unit). Examples of a low-molecular silazane compound include hexamethyldisilazane, hexaphenyldisilazane, dimethylaminotrimethylsilane, trisilazane, cyclotrisilazane, and 1,1,3,3,5,5-hexamethylcyclotrisilazane.

Examples of the alumina precursors include aluminum alkoxides, hydrolytic condensates thereof, water-soluble aluminum salts, and aluminum chelates. Examples of the zirconia precursors include zirconium alkoxides and hydrolytic condensates thereof. Examples of the titania precursors include titanium alkoxides and hydrolytic condensates thereof.

The liquid medium included in the coating agent is a solvent selected in accordance with a type of the matrix precursor and dissolves the matrix precursor. Examples of the liquid medium include water, alcohols, ketones, ethers, cellosolves, esters, glycol ethers, nitrogen-containing compounds, and sulfur-containing compounds.

Examples of the alcohols include methanol, ethanol, isopropanol, butanol, and diacetone alcohol. Examples of the ketones include acetone, methyl ethyl ketone, and methyl isobutyl ketone. Examples of the ethers include tetrahydrofuran and 1,4-dioxane. Examples of the cellosolves include methyl cellosolve and ethyl cellosolve. Examples of the esters include methyl acetate and ethyl acetate. Examples of the glycol ethers include ethylene glycol monoalkyl ether. Examples of the nitrogen-containing compounds include N,N-dimethylacetamide, N,N-dimethylformamide, and N-methylpyrrolidone. Examples of the sulfur-containing compounds include dimethyl sulfoxide. The liquid medium may be of a single type or a combination of two or more types.

The liquid medium preferably contains water, or in other words, is preferably water or a liquid mixture of water and another liquid medium. The other liquid medium is preferably an alcohol, and particularly preferably, methanol, ethanol, isopropyl alcohol, or butanol.

Further, the coating agent may include an acid catalyst that prompts hydrolysis and condensation of the matrix precursor. The acid catalyst is a component that prompts hydrolysis and condensation of the matrix precursor to form the anti-glare layer 14 promptly. The acid catalyst may be added for hydrolysis and condensation of a raw material (such as alkoxysilane) during the preparation of the matrix precursor before the preparation of the coating agent, or, may be added after the preparation of essential components. Examples of the acid catalyst include inorganic acids (such as nitric acid, sulfuric acid, and hydrochloric acid) and organic acids (such as formic acid, oxalic acid, acetic acid, monochloroacetic acid, dichloroacetic acid, and trichloroacetic acid).

Examples of a method for applying the coating agent include known wet coating processes (such as spray coating, spin coating, dip coating, dye coating, curtain coating, screen coating, inkjet coating, flow coating, gravure coating, bar coating, flexo coating, slit coating, and roll coating). The spray coating facilitates the formation of the uneven spots and is thus the preferred coating process.

Examples of a nozzle used for the spray coating include twin-fluid nozzles and single fluid nozzles. A droplet of the coating agent discharged from the nozzle normally has a diameter of 0.1 to 100 μm, and preferably 1 to 50 μm. When the diameter of the droplet is 0.1 μm or greater, uneven spots having a suitable anti-glare effect are promptly formed. When the diameter of the droplet is 100 μm or less, the formation of uneven spots having a suitable anti-glare effect is facilitated. The diameter of a droplet of the coating agent can be adjusted, for example, by changing the type of the nozzle, spraying pressure, and amount of liquid. For example, with a twin-fluid nozzle, the droplet becomes smaller as the spraying pressure increases, and the droplet becomes larger as the liquid amount increases. The diameter of the droplet corresponds to the Sauter mean diameter measured by a laser measurement instrument.

While applying the coating agent, the base material layer 13 has a surface temperature of, for example, 20° C. to 75° C., preferably 35° C. or greater, and further preferably 60° C. or greater. For example, it is preferred that a hydronic heating device be used for heating the base material layer 13.

The humidity while applying the coating agent is, for example, 40% to 70%, and preferably 50% or greater.

Next, the characteristic values of the glass article 10 in accordance with the present embodiment will be described.

The glass article 10 has a haze value of 15% or less and a clarity value of 9% or less. In this case, the glass article 10 preferably has a haze value of 7.5% or less and a clarity value of 8.5% or less.

Alternatively, the glass article 10 has a sparkle value of 0.02 or less and a clarity value of 9% or less. In this case, the glass article 10 preferably has a sparkle value of 0.017 or less and a clarity value of 8.5% or less.

Further, under any of the above conditions, the product of the haze value, the clarity value, and the sparkle value is preferably 0.5 or less, and further preferably 0.43 or less.

Haze Value

The haze value is a haze value (%) specified by JIS K7136 (2000). JIS K7136 (2000) corresponds to ISO 14782 and is directed to the same technical content.

Clarity Value

The clarity value is a ratio of the brightness of a specular reflection component to the brightness of a total reflection light obtained from brightness distribution data generated from an image, which is a reflection of a light source on the first main surface 11 of the glass article 10. The specific measurement method of the clarity value will now be described.

Figure 2:
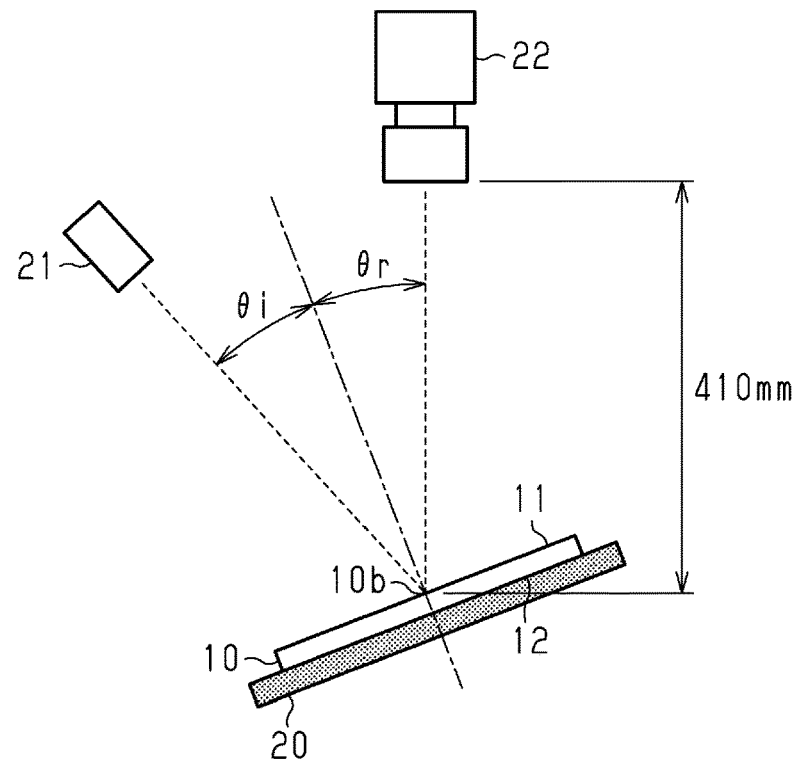
FIG. 2 is a schematic view illustrating measurement of the clarity value.

For example, the SMS-1000 (manufactured by Display-Messtechnik & Systeme) is used as a measurement device. As shown in FIG. 2, the glass article 10 is placed on a black glass plate 20, the glass plate having a thickness of 5 mm or greater, with the first main surface 11 located at an upper side. Further, a linear light source 21 and a light detector 22 are each arranged at respective positions opposing the first main surface 11 of the glass article 10. The light detector 22 includes a lens having a focal range of 16 mm. The linear light source 21 is located at a position inclined at a first angle θi toward one side (negative direction) from a direction parallel to the thickness-wise direction of the glass article 10 (direction orthogonal to first main surface 11). The first angle θi is, for example, 3°. The light detector 22 is located at a position inclined at a second angle θr toward the other side (positive direction) from the direction parallel to the thickness-wise direction of the glass article 10 so that the lens is located at a position separated by 410 mm from the first main surface 11. The linear light source 21 and the light detector 22 are arranged in the same plane, which is orthogonal to the first main surface 11 of the glass article 10.

Subsequently, light is emitted from the linear light source 21 toward the first main surface 11 of the glass article 10. Then, the light detector 22 obtains image data of the first main surface 11 of the glass article 10 and analyzes the image data to measure the brightness distribution data of the image reflected on the first main surface 11 in a range of $-5° \leq \theta(=\theta r-\theta i) \leq 5°$. To measure the brightness distribution data in a range of $-5° \leq \theta^*(=\theta r-\theta i) \leq 5°$, the light detector 22 is moved by increments of 0.1° on the above plane, which is orthogonal to the first main surface 11 of the glass article 10, and image data is obtained at each position. The clarity value is calculated from equation (1) based on the brightness of total refection light and the brightness of specular reflection component obtained from the brightness distribution data.

clarity value (%)=(brightness of specular reflection component)/(brightness of total refection light)=100    (1)

For example, the SMS-1000 (manufactured by Display-Messtechnik & Systeme) may be used as the light detector 22. The brightness distribution data may be measured, for example, by the SMS-1000 in the reflection distribution measurement mode (software "Sparkle measurement system"). The brightness of specular reflection component refers to a brightness in a range of $-0.1° \leq \theta^*(=\theta r-\theta i) \leq 0.1°$.

Sparkle Value

The sparkle value is a value obtained as described below. First, a single-colored planar light source is disposed opposing the second main surface 12 of the glass article 10, and a pattern mask (pixel size of 10×40 μm), of which the pixel size is 10×40 μm and 500 ppi, is arranged between the glass article 10 and the planar light source. The glass article 10 is imaged from a position opposing the first main surface 11 to include the first main surface 11 of the glass article and a top surface of the pattern mask in a depth of field with a permissible circle of confusion having the diameter of 53 μm. Image data obtained through the imaging is analyzed to calculate an average value and a standard deviation of a pixel brightness of the pattern mask. Consequently, the sparkle value is obtained by dividing the standard deviation of the pixel brightness of the pattern mask by the average value of the pixel brightness of the pattern mask. The specific measurement method of the sparkle value will now be described.

Figure 3:
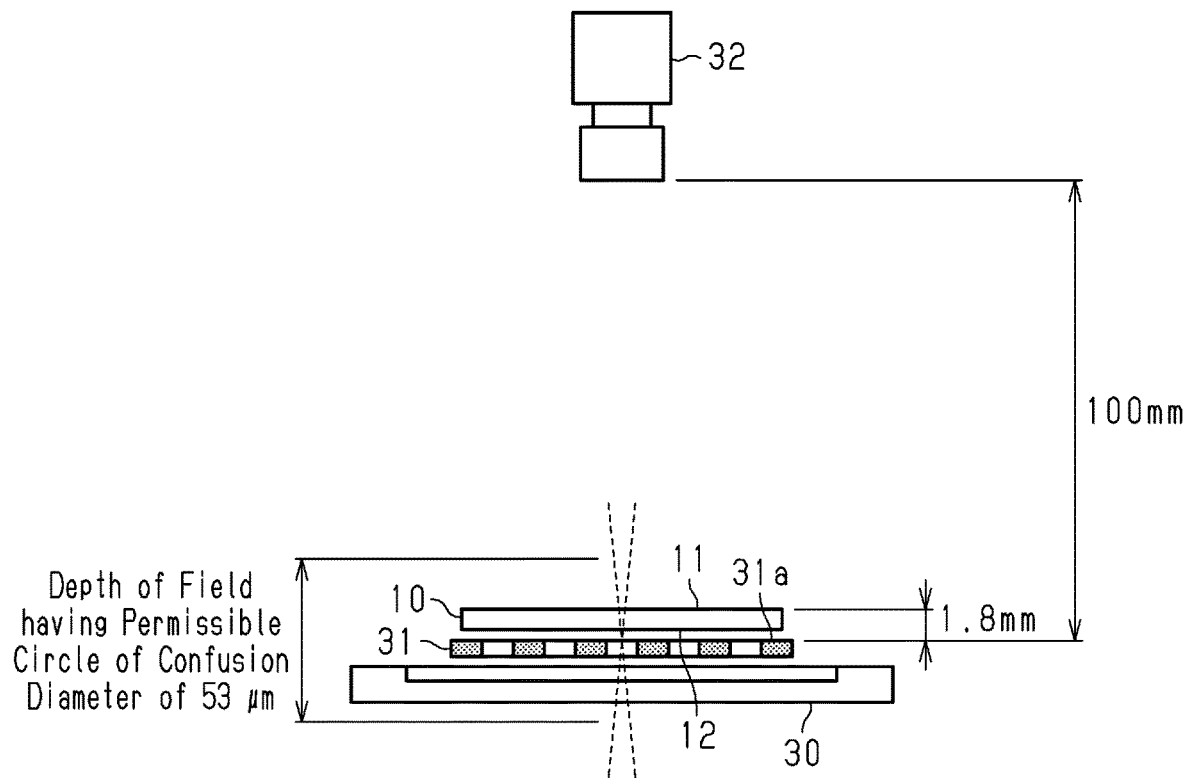
FIG. 3 is a schematic view illustrating measurement of the sparkle value.
Figure 4:
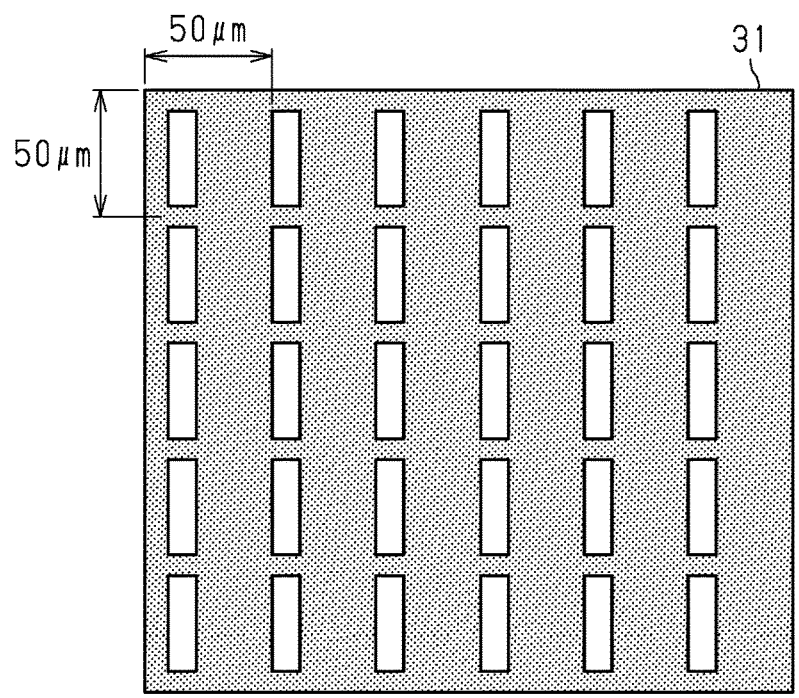
FIG. 4 is a schematic view of a pattern mask.

For example, the SMS-1000 (manufactured by Display-Messtechnik & Systeme) is used as a measurement device. As shown in FIG. 3, a pattern mask 31 is placed on a planar light source 30, and the glass article 10 is placed on the pattern mask 31 so that the second main surface 12 faces the pattern mask 31. As shown in FIG. 4, the pattern mask 31 is a 500 ppi pattern mask having a pixel pitch of 50 μm.

Further, as shown in FIG. 3, a light detector 32 is disposed at a position opposing the first main surface 11 of the glass article 10. The light detector 32 is set to have a permissible circle of confusion having the diameter of 53 μm. The glass article 10, the pattern mask 31, and the light detector 32 are arranged so that the first main surface 11 of the glass article 10 and a top surface 31a of the pattern mask 31 will be located in the depth of field when the light detector 32 has a permissible circle of confusion having the diameter of 53 μm (forward depth of field and rearward depth of field).

As one example of the specific arrangement, the focal range of the light detector 32 is set to 100 mm, and the lens aperture diameter is set to 4.5 mm. The light detector 32 has a sensor size of ⅓ type and a pixel size of 3.75×3.75 μm. Then, the pattern mask 31 is arranged so that the top surface 31a is located at the focal position, and the glass article 10 is arranged so that the distance between the top surface 31a of the pattern mask 31 and the first main surface 11 is 1.8 mm. When the glass article 10, the pattern mask 31, and the light detector 32 are arranged so that the first main surface 11 of the glass article 10 and the top surface 31a of the pattern mask 31 are located in the depth of field of the light detector 32 with a permissible circle of confusion having the diameter of 53 μm, the measured sparkle value is highly correlated with human visual image recognition (human eye structure, eye movement, and image recognition through brain processing).

Subsequently, light is emitted from the planar light source 30 toward the glass article 10 through the pattern mask 31, and the light detector 32 obtains image data of the first main surface 11 of the glass article 10. The obtained image data has a resolution of 120 pixels for each pixel of the pattern mask 31. The obtained image data is analyzed to calculate the pixel brightness of each pixel of the pattern mask 31.

Then, the standard deviation of the pixel brightness and the average value of the pixel brightness between pixels are obtained. The sparkle value is calculated from equation (2) based on the obtained standard deviation and average value of the pixel brightness between pixels.

$$\text{sparkle value} = (\text{standard deviation of pixel brightness of pattern mask})/(\text{average value of pixel brightness of pattern mask}) \quad (2)$$

The standard deviation and the average value of the pixel brightness between pixels may be measured, for example, by using the SMS-1000 in the sparkle measurement mode (software "Sparkle measurement system").

Next, the operation of the present embodiment will be described.

The glass article 10 of the present embodiment has a haze value of 15% or less, preferably 7.5% or less, and a clarity value of 9% or less, preferably 8.5% or less. Alternatively, the glass article 10 of the present embodiment has a sparkle value of 0.02 or less, preferably 0.017 or less, and a clarity value of 9% or less, preferably 8.5% or less. It is preferred that the product of the haze value, clarity value, and sparkle value be 0.5 or less.

This allows a person to perceive that an image is easily viewed through the glass article. That is, the glass article allows an image to be perceived as easy to view through human visual image recognition (human eye structure, eye movement, and image recognition through brain processing).

The haze value, clarity value, and sparkle value of the glass article 10 can be adjusted, for example, by changing a formation condition of the anti-glare layer 14. For example, when the anti-glare layer 14 is formed by spray coating a coating agent, an increase in the humidity during the application of the coating agent will result in a tendency of both of the haze value and clarity value to decrease. A decrease in the diameter of droplets of the coating agent, for example, by decreasing the nozzle diameter will result in a tendency of both of the haze value and clarity value to decrease. A decrease in the amount of coating agent applied per unit area of the surface of the anti-glare layer 14 will result in a tendency of the haze value to decrease. An increase in the surface temperature of the base material layer 13 (e.g. 40° C. or greater) will result in a tendency of the sparkle value to decrease. In one example, if the anti-glare layer 14 is formed under a condition in which the humidity is 52% or greater and the surface temperature of the base material layer 13 is 20° C. or greater, the glass article 10 easily obtains the haze value of 15% or less, the clarity value of 9% or less, and the product of the haze value, clarity value, and sparkle value of 0.5 or less. In addition, the haze value, clarity value, and sparkle value can be decreased by changing the type of the matrix precursor or the solvent included in the coating agent or changing the application process to one other than spray coating.

The present embodiment has the advantages described below.

(1) The glass article 10 has a haze value of 15% or less and a clarity value of 9% or less. This structure allows a person to perceive that an image is easily viewed through the glass article. That is, the glass article allows an image to be easily viewed through human visual image recognition (human eye structure, eye movement, and image recognition through brain processing).

(2) The glass article 10 has a sparkle value of 0.02 or less and the clarity value of 9% or less. This structure allows a person to perceive that an image is easily viewed through the glass article.

(3) The product of the haze value, clarity value, and sparkle value is 0.5 or less. In this case, advantages (1) and (2) are further effectively obtained.

(4) The glass article 10 includes the base material layer 13 made of glass and the anti-glare layer 14 arranged on the base material layer 13 at a position close to the first main surface 11. The anti-glare layer 14 has an uneven structure that includes bulged portions and flat portions arranged therebetween. In this case, advantages (1) and (2) are further effectively obtained.

The present embodiment may be modified as described below.

The anti-glare layer 14 does not have to have a structure in which uneven spots are scattered. For example, the anti-glare layer 14 may have an uneven structure formed through any other process such as blasting or etching.

The anti-glare layer 14 may be formed on the second main surface 12 in addition to the first main surface 11 of the glass article 10.

Any other layer such as an antireflection layer or an antifouling layer may be formed at least between the base material layer 13 and the anti-glare layer 14 or on the anti-glare layer 14.

As long as the above haze value and clarity value are obtained, the glass article 10 does not have to include the anti-glare layer 14.

As long as the above haze value and clarity value are obtained or the above sparkle value and clarity value are obtained, the transparent article does not have to be the glass article 10 and may be, for example, a resin article. In this case, the base material layer 13 is formed from a transparent material.

EXAMPLES

The above embodiment will now be described in further detail using experimental examples. The present invention is not limited to these experimental examples.

Experimental Examples

As shown in Tables 1 and 2, glass articles having different haze values, clarity values, and sparkle values were prepared for experimental examples 1 to 9. The haze values, clarity values, and sparkle values were differentiated from one another by changing the formation condition of the anti-glare layer. The method for manufacturing the glass articles of experimental examples 1 to 9 and the specific measurement method of the haze values, clarity values, and sparkle values will now be described.

Experimental Examples 1 to 9

An anti-glare layer was formed by applying a coating agent to the surface of a glass base material with a spray coating device having the nozzle diameter shown in Tables 1 and 2. The coating agent was prepared by dissolving a precursor of the anti-glare layer (tetraethoxysilane) in a liquid medium including water. The glass base material was a glass sheet having the thickness of 1.3 mm (T2X-1, manufactured by Nippon Electric Glass Co., Ltd). The surface temperature of the glass base material, the ambient humidity, and the amount of the coating agent applied per unit area of the glass base material were as shown in Tables 1 and 2.

Haze Value

The haze values (%) were measured in a manner pursuant to JIS K7136 (2000).

Clarity Value

As shown in FIG. 2, the clarity values (%) were measured using the SMS-1000 (manufactured by Display-Messtechnik & Systeme) in the reflection distribution measurement mode. A lens with a focal range of 16 mm was used, the first angle $\theta i$ was set to 3°, and the distance from an irradiated portion 10b of the first main surface 11 to the lens was set to 410 mm.

Sparkle Value

As shown in FIG. 3, the sparkle values were measured using the SMS-1000 (Display-Messtechnik & Systeme) in the sparkle measurement mode. The SMS-1000 had a CCD camera having 1296×966 pixels, a sensor size of a ⅓ type, and a pixel size of 3.75×3.75 μm. The lens was set to have the focal range of 100 mm, an aperture diameter of 4.5 mm, a magnification ratio of 1:1, and a permissible circle of confusion diameter of 53 μm. Further, the pattern mask was arranged to position the top surface at the focal position of the lens, and the glass articles of the experimental examples were arranged to position the second main surface 300 μm above the top surface of the pattern mask.

Sensory Evaluation

Twenty panelists observed the first main surfaces of the glass articles of the experimental examples in a photopic vision and ranked the glass articles in the order of easiness to view images through the glass articles. Then, the experimental examples ranked as any one of first to third places by fifteen or more of the twenty panelists were evaluated as A, the experimental examples ranked as any one of first to sixth places by fifteen or more of the twenty panelists was evaluated as B, and the other experimental examples were evaluated as C. The results are shown in Tables 1 and 2. Typically, the easiness to view an image through a glass article is determined from various viewpoints such as clarity, anti-glare characteristics, low-glare characteristics, whether or not there is a reflection In the present evaluation, each panelist determined the easiness of viewing an image comprehensively based on personal perceptions without focusing on certain viewpoints or prioritizing certain viewpoints.

TABLE 1

|  | Experimental Example 1 | Experimental Example 2 | Experimental Example 3 | Experimental Example 4 | Experimental Example 5 |
|---|---|---|---|---|---|
| Nozzle Diameter (mm) | 0.6 | 0.4 | 0.4 | 0.6 | 0.6 |
| Surface Temperature of Glass Base Material (° C.) | 20 | 71 | 71 | 20 | 20 |
| Ambient Humidity (%) | 67 | 52 | 52 | 52 | 67 |
| Amount of Coating Agent Applied per Unit Area of Glass Material | 69 | 31 | 38 | 42 | 52 |
| Haze Value (H) | 5.32 | 5.52 | 6.88 | 13.98 | 3.85 |
| Clarity Value (C) | 4.3 | 6.7 | 3.5 | 3.3 | 8.4 |
| Sparkle Value (S) | 0.0163 | 0.0116 | 0.0123 | 0.0157 | 0.0131 |
| H × C × S | 0.37 | 0.43 | 0.30 | 0.72 | 0.42 |
| Sensory Evaluation | A | A | A | B | A |

TABLE 2

|  | Experimental Example 6 | Experimental Example 7 | Experimental Example 8 | Experimental Example 9 |
|---|---|---|---|---|
| Nozzle Diameter (mm) | 0.6 | 0.6 | 0.4 | 0.6 |
| Surface Temperature of Glass Base Material (° C.) | 71 | 71 | 71 | 20 |
| Ambient Humidity (%) | 52 | 52 | 52 | 52 |
| Amount of Coating Agent Applied per Unit Area of Glass Material | 52 | 63 | 63 | 52 |
| Haze Value (H) | 9.17 | 12.84 | 9.87 | 15.72 |
| Clarity Value (C) | 5.4 | 4.0 | 2.8 | 4.0 |
| Sparkle Value (S) | 0.009 | 0.0135 | 0.0174 | 0.0215 |
| H × C × S | 0.45 | 0.69 | 0.48 | 1.35 |
| Sensory Evaluation | B | B | B | C |

As shown in Tables 1 and 2, experimental examples 1 to 8, which had the haze value of 15% or less and the clarity value of 9% or less, were evaluated as A or B in the sensory evaluation. This indicates that a person perceives that an image is easily viewed through the glass article. Further, experimental examples 1 to 8, which have the sparkle value of 0.02 or less and the clarity value of 9% or less, were evaluated as A or B in the sensory evaluation. This indicates that a person perceives that an image is easily viewed through the glass article. Moreover, as the product of the haze value, clarity value, and sparkle value decreases, the sensory evaluation has a tendency to be higher.

Next, technical concepts obtained from the above embodiment and the modified examples will be described.

(1) The transparent article includes a base material layer formed from a transparent material and an anti-glare layer arranged on the base material layer at a position close to the first main surface.

(2) The anti-glare layer of the transparent article has an uneven structure that includes bulged portions and flat portions arranged therebetween.

(3) A method for manufacturing a transparent article including a base material layer, which is formed from a transparent material, and an anti-glare layer, the method comprising forming the anti-glare layer on a surface of the base material layer through a spray coating process, wherein the forming the anti-glare layer is performed with a surface temperature of the base material layer set to 40° C. or greater.

DESCRIPTION OF REFERENCE CHARACTERS 10) glass article; 11) first main surface; 12) second main surface; 13) base material layer; 14) anti-glare layer; 20) black glass plate; 21) linear light source; 22, 32) light detector; 30) planar light source; 31) pattern mask.

The invention claimed is:

1. A transparent article including a first main surface located at a front side and a second main surface located at a rear side, the transparent article comprising:
   a haze value of 15% or less that is specified by ISO 14782 (1999); and a clarity value of 9% or less,
   wherein the clarity value is a ratio of a brightness of a specular reflection component to a brightness of a total refection light obtained from brightness distribution data of an image, which is a reflection of a light source on the first main surface of the transparent article, and further wherein the transparent article has a predetermined sparkle value,
   a value obtained by multiplying a product of the haze value and the clarity value by the sparkle value is 0.5 or less, and
   the sparkle value is a value obtained by arranging a planar light source at a position opposing the second main surface of the transparent article, arranging a pattern mask of 500 ppi between the transparent article and the planar light source, imaging the transparent article from a position opposing the first main surface so that the first main surface of the transparent article and a top surface of the pattern mask are included in a depth of field having a permissible circle of confusion diameter of 53 μm, calculating an average value and a standard deviation of a pixel brightness of the pattern mask by analyzing image data obtained through the imaging, and dividing the standard deviation by the average value.

2. A transparent article including a first main surface located at a front side and a second main surface located at a rear side, the transparent article comprising:
   a haze value of 15% or less that is specified by ISO 14782 (1999); and a clarity value of 9% or less,
   wherein the clarity value is a ratio of a brightness of a specular reflection component to a brightness of a total refection light obtained from brightness distribution data of an image, which is a reflection of a light source on the first main surface of the transparent article, and further wherein the transparent article has a sparkle value of 0.02 or less that is obtained by arranging a planar light source at a position opposing the second main surface of the transparent article, arranging a pattern mask of 500 ppi between the transparent article and the planar light source, imaging the transparent article from a position opposing the first main surface so that the first main surface of the transparent article and a top surface of the pattern mask are included in a depth of field having a permissible circle of confusion diameter of 53 μm, calculating an average value and a standard deviation of a pixel brightness of the pattern mask by analyzing image data obtained through the imaging, and dividing the standard deviation by the average value.

3. A transparent article including a first main surface located at a front side and a second main surface located at a rear side, the transparent article comprising:
   a sparkle value of 0.02 or less; and
   a clarity value of 9% or less, wherein
   the clarity value is a ratio of a brightness of a specular reflection component to a brightness of a total refection light obtained from brightness distribution data of an image, which is a reflection of a light source on the first main surface of the transparent article, and
   the sparkle value is a value obtained by arranging a planar light source at a position opposing the second main surface of the transparent article, arranging a pattern mask of 500 ppi between the transparent article and the planar light source, imaging the transparent article from a position opposing the first main surface so that the first main surface of the transparent article and a top surface of the pattern mask are included in a depth of field having a permissible circle of confusion diameter of 53 μm, calculating an average value and a standard deviation of a pixel brightness of the pattern mask by analyzing image data obtained through the imaging, and dividing the standard deviation by the average value.

4. The transparent article according to claim 3, wherein the transparent article has a predetermined haze value that is specified by ISO 14782 (1999), a value obtained by multiplying a product of the clarity value and the sparkle value by the haze value is 0.5 or less.

* * * * *